United States Patent [19]

Tomalia et al.

[11] Patent Number: 4,568,737

[45] Date of Patent: Feb. 4, 1986

[54] DENSE STAR POLYMERS AND DENDRIMERS

[75] Inventors: Donald A. Tomalia, Midland; James R. Dewald, Bay City, both of Mich.

[73] Assignee: The Dow Chemical Company, Midland, Mich.

[21] Appl. No.: 641,807

[22] Filed: Aug. 17, 1984

Related U.S. Application Data

[63] Continuation-in-part of Ser. No. 456,226, Jan. 1, 1983, Pat. No. 4,507,466, and a continuation-in-part of Ser. No. 565,686, Dec. 27, 1983.

[51] Int. Cl.$^4$ .............................................. C08G 69/00
[52] U.S. Cl. ..................................... 528/332; 525/451; 528/310; 528/328; 528/363; 528/425
[58] Field of Search ............... 528/332, 363, 310, 328, 528/331, 425; 525/451; 560/155, 169, 171, 215; 564/153, 155, 468, 509

[56] References Cited

U.S. PATENT DOCUMENTS

| | | | |
|---|---|---|---|
| 3,528,928 | 9/1970 | Rushton | 252/341 |
| 3,578,643 | 5/1971 | Wood et al. | 528/363 |
| 3,580,891 | 5/1971 | Rainer | 528/310 |
| 3,773,739 | 11/1973 | Bonvicini et al. | 528/310 |
| 4,102,827 | 7/1978 | Rembaum et al. | 260/823 |
| 4,289,872 | 9/1981 | Denkewalter et al. | 528/328 |
| 4,435,548 | 3/1984 | Tomalia et al. | 528/332 |
| 4,507,466 | 3/1985 | Tomalia et al. | 528/363 |

OTHER PUBLICATIONS

Bauer et al. Rubber Chem. Tech., 1978, 51 (3), pp. 406-436.
Bywater-Adv. Poly. Sci, 30, (1979), pp. 89-116.
Luxton et al. Polymer (1978), vol. 19, pp. 1320-1324.
Yen et al-Poly. Sci. Tech., 2 (1973) pp. 291-312.

*Primary Examiner*—Harold D. Anderson
*Attorney, Agent, or Firm*—M. S. Jenkins

[57] ABSTRACT

Dense star polymers having terminal group densities greater than conventional star polymers exhibit greater and more uniform reactivity than their corresponding conventional star polymers. For example, a third generation, amine-terminated polyamidoamine dense star polymer prepared from ammonia, methyl acrylate and ethylenediamine has $1.24 \times 10^{-4}$ amine moieties per unit volume (cubic Angstrom units) in contrast to the $1.58 \times 10^{-6}$ amine moieties per unit volume contained by a conventional star polymer. Such dense star polymers are useful as demulsifiers for oil/water emulsions, wet strength agents in the manufacture of paper, and agents for modifying viscosity in aqueous formulations such as paints.

7 Claims, No Drawings

DENSE STAR POLYMERS AND DENDRIMERS

CROSS-REFERENCE TO RELATED APPLICATIONS

This application is a continuation-in-part of application Ser. No. 456,226, filed on Jan. 1, 1983, now U.S. Pat. No. 4,507,466, and a continuation-in-part of application Ser. No. 565,686, filed on Dec. 27, 1983.

BACKGROUND OF THE INVENTION

This invention relates to a novel class of branched polymers containing dendritic branches having functional groups uniformly distributed on the periphery of such branches. This invention also relates to processes for preparing such polymers as well as applications therefore.

Organic polymers are generally classified in a structural sense as either linear or branched. In the case of linear polymers, the repeating units (often called mers) are divalent and are connected one to another in a linear sequence. In the case of branched polymers, at least some of the mers possess a valency greater than 2 such that the mers are connected in a nonlinear sequence. The term "branching" usually implies that the individual molecular units of the branches are discrete from the polymer backbone, yet have the same chemical constitution as the polymer backbone. Thus, regularly repeating side groups which are inherent in the monomer structure and/or are of different chemical constitution than the polymer backbone are not considered as branches, e.g., dependent methyl groups of linear polypropylene. To produce a branched polymer, it is necessary to employ an initiator, a monomer, or both that possess at least three moieties that function in the polymerization reaction. Such monomer or initiators are often called polyfunctional. The simplest branched polymers are the chain branched polymers wherein a linear backbone bears one or more essentially linear pendant groups. This simple forms of branching, often called comb branching, may be regular wherein the branches are uniformly and regularly distributed on the polymer backbone or irregular wherein the branches are distributed in nonuniform or random fashion on the polymer backbone. See T. A. Orofino, *Polymer*, 2, 295-314 (1961). An example of regular comb branching is a comb branched polystyrene as described by T. Altores et al. in *J. Polymer Sci., Part A*, Vol. 3, 4131-4151 (1965) and an example of irregular comb branching is illustrated by graft copolymers as described by Sorenson et al. in "Preparative Methods of Polymer Chemistry", 2nd Ed., Interscience Publishers, 213-214 (1968).

Another type of branching is exemplified by cross-linked or network polymers wherein the polymer chains are connected via tetravalent compounds, e.g., polystyrene molecules bridged or cross-linked with divinylbenzene. In this type of branching, many of the individual branches are not linear in that each branch may itself contain groups pendant from a linear chain. More importantly in network branching, each polymer macromolecule (backbone) is cross-linked at two or more sites to two other polymer macromolecules. Also the chemical constitution of the cross-linkages may vary from that of the polymer macromolecules. In this so-called cross-linked or network branched polymer, the various branches or cross-linkages may be structurally similar (called regular cross-linked) or they may be structurally dissimilar (called irregularly cross-linked). An example of regular cross-linked polymers is a ladder-type poly(phenylsilsesquinone) as described by Sorenson et al., supra, at page 390. The foregoing and other types of branched polymers are described by H. G. Elias in *Macromolecules*, Vol. I, Plenum Press, N.Y. (1977).

More recently, there have been developed polymers having so-called star structured branching wherein the individual branches radiate out from a nucleus and there are at least 3 branches per nucleus. Such star branched polymers are illustrated by the polyquaternary compositions described in U.S. Pat. Nos. 4,036,808 and 4,102,827. Star branched polymers prepared from olefins and unsaturated acids are described in U.S. Pat. NO. 4,141,847. The star branched polymers offer several advantages over polymers having other types of branching. For example, it is found that the star branched polymers may exhibit higher concentrations of functional groups thus making them more active for their intended purpose. In addition, such star branched polymers are often less sensitive to degradation by shearing which is a very useful property in formulations such as paints, in enhanced oil recovery and other viscosity applications. Additionally, the star branched polymers have relatively low intrinsic viscosities even at high molecular weight.

While the star branched polymers offer many of the aforementioned advantages over polymers having more conventional branching, it is highly desirable to provide polymers which exhibit even greater concentrations of functional groups per unit volume of the polymer macromolecule as well as a more uniform distribution of such functional groups in the exterior regions of the macromolecule. In addition, it is often desirable to provide polymers having macromolecule configurations that are more spheroidal and compact than are the star branched polymers.

SUMMARY OF THE INVENTION

In its broadest aspect, this invention is a dense star polymer having at least one branch (hereinafter called a core branch) emanating from a core, said branch having at least one terminal group provided that (1) the ratio of terminal groups to the core branches is more than one, preferably two or greater, (2) the density of terminal groups per unit volume in the polymer is at least 1.5 times that of a conventional star polymer having similar core and monomeric moieties and a comparable molecular weight and number of core branches, each of such branches of the conventional star polymer bearing only one terminal group, and (3) a molecular volume that is no more than about 60 percent of the molecular volume of said conventional star polymer as determined by dimensional studies using scaled Corey-Pauling molecular models. For purposes of this invention, the term "dense" as it modifies "star polymer" means that it has a smaller molecular volume than a conventional star polymer having the same molecular weight. The conventional star polymer which is used as the base for comparison with the dense star polymer is one that has the same molecular, same core and monomeric components and same number of core branches as the dense star polymer. In addition while the number of terminal groups is greater for the dense star polymer molecule than in the conventional star polymer molecule, the chemical structure of the terminal groups is the same.

In a somewhat more limited and preferred aspect, this invention is a polymer having a novel ordered star branched structure (herein called starburst structure). Hereinafter this polymer having a starbust structure is called a dendrimer. Thus, a "dendrimer" is a polymer having a polyvalent core that is covalently bonded to at least two ordered dendritic (tree-like) branches which extend through at least two generations. As an illustration, an ordered second generation dendritic branch is depicted by the following configuration:

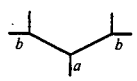

wherein "a" represents the first generation and "b" represents the second generation. An ordered, third generation dendritic branch is depicted by the following configuration:

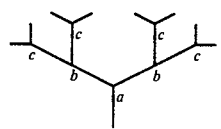

wherein "a" and "b" represent the first and second generation, respectively, and "c" represents the third generation. A primary characteristic of the ordered dendritic branch which distinguishes it from a conventional branches of conventional polymers is the uniform or essentially symmetrical character of the branches as is shown in the foregoing illustrations. In addition, with each new generation, the number of terminal groups on the dendritic branch is an exact multiple of the number of terminal groups in the previous generation.

Another aspect of this invention is a process for producing the dense star polymer comprising the steps of
(A) contacting
  (1) a core compound having at least one nucleophilic or one electrophilic moiety (hereinafter referred to in the alternative as N/E moieties) with
  (2) an excess of a first organic coreactant having (a) one moiety (hereinafter called a core reactive moiety) which is reactive with the N/E moieties of the core compound and (b) an N/E moiety which does not react with the N/E moiety of the core under conditions suffifient to form a core adduct wherein each N/E moiety of the core compound has reacted with the core reactive moiety of a different molecule of the first coreactant;
(B) contacting
  (1) the core adduct having at least twice the number of N/E moieties as the core compound with
  (2) an excess of a second organic coreactant having (a) one moiety (hereinafter called an adduct reactive moiety) which will react with the N/E moieties of the core adduct and (b) an N/E moiety which does not react with the N/E moiety of the core adduct under conditions sufficient to form a first generation adduct having a number of N/E moieties that are at least twice the number of N/E moieties in the core adduct; and
(C) contacting the first generation adduct with an excess of a third organic coreactant having one moiety that is reactive with the N/E moieties of the first generation adduct and an N/E moiety that does not react with the N/E moieties of the first generation adduct under conditions sufficient to form a second generation dendrimer. In the foregoing process, the first coreactant differs from the second coreactant, and the second coreactant differs from the third coreactant, but the first and third coreactants may be the same or different compounds. The third and higher generation dendrimers are formed by repeating steps (B) and (C) of the aforementioned process.

Other aspects of this invention are methods for using the dense star polymer in such applications as demulsifiers for oil/water emulsions, wet strength agents in the manufacture of paper, agents for modifying viscosity in aqueous formulations such as paints and the like. For example, in a demulsification method, an emulsion of oil and water is contacted with a demulsifying amount of the dense star polymer under conditions sufficient to cause phase separation.

The dense star polymers of the present invention exhibit the following properties which are unique or are superior to similar properties of conventional star branched polymers and other branched polymers having similar molecular weight and terminal groups:
(a) greater branch density;
(b) greater terminal group density;
(c) greater accessibility of terminal groups to chemically reactive species; and
(d) lower viscosity.

DETAILED DESCRIPTION OF ILLUSTRATIVE EMBODIMENTS

In the dense star polymers of the present invention, the core is covalently bonded to at least one core branch, preferably at least two, most preferably at least three, core branches with each core branch having a calculated length of at least 3 Angstrom units (A), preferably at least 4 A, most preferably at least 6 A. These polymers preferably have an average of at least 2, more preferably at least 3 and most preferably at least 4 terminal groups per polymer molecule. Preferably, the core branches have a dendritic character, most preferably an ordered dendritic character as defined hereinafter.

The dense star polymers of this invention preferably have two-dimensional molecular diameters in the range from about 12 to about 2000 Angstrom units (A), more preferably from about 25 to about 500 A and most preferably from about 250 A. For the purpose of this invention, a two-dimensional molecular diameter is determined by the following electron microscopic method. First, the terminal groups of dendrimers are connected to anionic moieties (e.g., by hydrolysis of the terminal ester moieties of polyamidoamine dendrimer in half generation state). The anionic dendrimer molecules are then neutralized with stoichiometric amounts of alkali metal hydroxide. A dilute aqueous solution (e.g., about 0.5 weight percent of the neutralized dendrimer in water) of the dendrimer is placed on a beryllium grid (~1.5 millimeter diameter puddle) and allowed to evaporate. The dendrimer often exhibits dendritic-like crystalline growth during the evaporation process. The diameter of the dry dendrimer molecules in two-dimensional state are then measured by electron microscopy and found to correspond closely, e.g., within 15 percent, to the diameters predicted by scaled Corey-Pauling molecular models. Such measurements are readily made using a *JEM*-1200 *EX Electron Microscope* sold by JEOL Corporation using CTEM techniques on a beryllium grid coated with 50 A carbon.

The dense star polymers of this invention preferably have three-dimensional molecular diameters in the range from about 6 to about 1000, more preferably from about 10 to about 250, most preferably from about 25 to about 125 Angstrom units. For the purposes of this invention, a three-dimensional molecular diameter is determined by calculating hydrodynamic diameters using the following Hester-Mitchell relationship, R. D. Hester et al., *J. Poly Sci.*, Vol. 18, p. 1727 (1980).

$$d = \left[\frac{240}{\pi N}\right]^{\frac{1}{3}} [M(\eta)]^{\frac{1}{3}}$$

wherein d is the hydrodynamic diameter in Angstrom units; N is $6.02 \times 10^{23}$; M is number average molecular weight of the dendrimer; and n intrinsic viscosity of the dense star polymer in deciliters per gram at 25° C.

In preferred dense star polymers, the terminal groups are functional groups that are sufficiently reactive to undergo addition or substitution reactions. Examples of such functional groups include amino, hydroxy, mercapto, carboxy, alkenyl, ally, vinyl, amido, halo, urea, oxiranyl, aziridinyl, oxazolinyl, imidazolinyl, sulfonato, phosphonato, isocyanato and isothiocyanato. The dense star polymers differ from conventional star or star-branched polymers in that the dense star polymers have a greater concentration of terminal groups per unit of molecular volume than do conventional star polymers having an equivalent number of core branches and an equivalent core branch length. Thus, the density of terminal groups per unit volume in the dense star polymer is at least about 1.5 times the density of terminal groups in the conventional star polymer, preferably at least 5 times, more preferably at least 10 times, most preferably from about 15 to about 50 times. The ratio of terminal groups per core branch in the dense polymer is preferably at least 2, more preferably at least 3, most preferably from about 4 to about 1024. Preferably, for a given polymer molecular weight, the molecular volume of the dense star polymer is less than 50 volume percent, more preferably from about 16 to about 50, most preferably from about 7 to about 40 volume percent of the molecular volume of the conventional star polymer.

In the preferred polyamidoamine dense star polymers, the density of terminal (primary) amine moieties in the polymer is readily expressed as the molar ratio of primary amine moieties to the total of secondary and tertiary amine moieties. In such polymers this 1° amine:(2° amino+3° amine) is preferably from about 0.37:1 to about 1.33:1, more preferably from about 0.69:1 to about 1.2:1, most preferably from about 1.1:1 to about 1.2:1.

The preferred dendrimers of the present invention are characterized as having a polyvalent core that is covalently bonded to at least two ordered dendritic branches which extend through at least two generations. Such ordered branching can be illustrated by the following sequence wherein G indicates the number of generations:

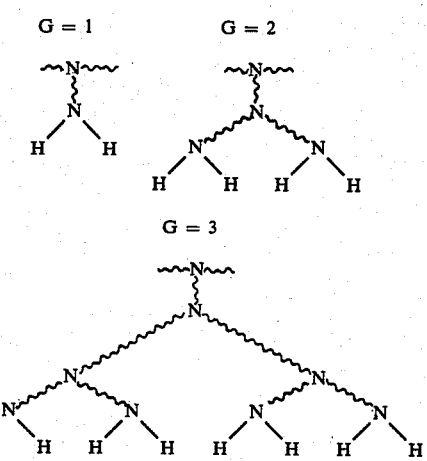

Mathematically, the relationship between the number of terminal groups on a dendritic branch and the number of generations of the branch can be represented as follows:

$$\text{\# of terminal groups per dendritic branch} = \frac{N_r^G}{2}$$

wherein G is the number of generations and $N_r$ is the repeating unit multiplicity which is at least 2 as in the case of amines. The total number of terminal groups in the dendrimer is determined by the following:

$$\text{\# of terminal groups per dendrimer} = \frac{N_c N_r^G}{2}$$

wherein G and $N_r$ are as defined before and $N_c$ represents the valency (often called core functionality) of the core compound. Accordingly, the dendrimers of the present invention can be represented in its component parts as follows:

$$(\text{Core})\left[(\text{Repeat Unit})\frac{N_r^G - 1}{N_r - 1}\left(\begin{array}{c}\text{Terminal}\\\text{Moiety}\end{array}\right)\frac{N_r^G}{2}\right]_{N_c}$$

wherein the Core, Terminal Moiety, G and $N_c$ are as defined before and the Repeat Unit has a valency or functionality of $N_r+1$ wherein $N_r$ is as defined before.

An illustration of a functionally active dendrimer of a ternary or trivalent core which has three ordered, second generation dendritic branches is depicted by the following configuration:

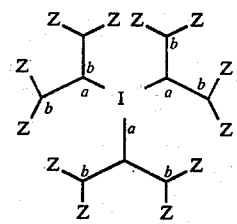

wherein I is a trivalent core atom or molecule having a covalent bond with each of the three dendritic branches, Z is a terminal moiety and "a" and "b" are as defined hereinbefore. An example of such a ternary dendrimer is polyamidoamine represented by the following structural formula:

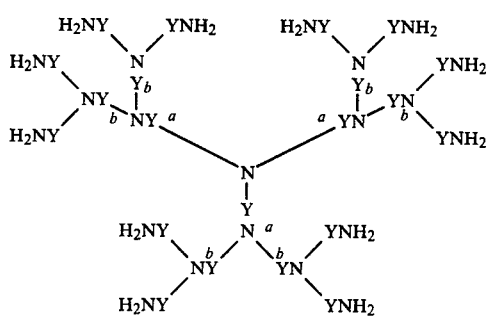

wherein Y represents a divalent amide moiety such as

and "a" and "b" indicate first and second generations, respectively. In these two illustrations, $N_c$ is 3 and N is 2. In the latter of the two illustrations, the Repeat Unit is YN. While the foregoing configuration and formula illustrate a trivalent core, the core atom or molecule may be any monovalent or monofunctional moiety or any polyvalent or polyfunctional moiety, preferably a polyvalent or polyfunctional moiety having from 2 to about 2300 valence bonds or functional sites available for bonding with the dendritic branches, most preferably from about 2 to about 200 valence bonds or functional sites. In cases wherein the core is a monovalent or monofunctional moiety, the dense star has only one core branch and must be compared with a linear polymer in order to determine appropriate terminal group density and molecular volume. Accordingly, this dense star must have at least 2 generations in order to exhibit the desired density of terminal groups. Also, Y may be any other divalent organic moiety such as alkylene, alkylene oxide, alkyleneamine, and the like, with the depicted amide moiety being the most preferred. In addition to amine, the terminal groups of the dendrimer may be any functionally active moiety that can be used to propagate the dendritic branch to the next generation. Examples of such other moieties include carboxy, aziridinyl, oxazolinyl, haloalkyl, oxiranyl, hydroxy and isocyanato, with amine or carboxylic ester moieties being preferred. While the dendrimers preferably have dendritic branches having 2 to 6 generations, dendrimers having dendritic branches up to 12 generations are suitably made and employed in the practice of this invention.

More preferably, the amidoamine dendrimers of this invention are represented by the formula:

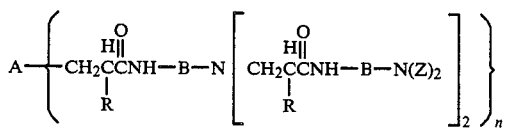

wherein A is a n-valent core derived from a nucleophilic compound, R is hydrogen or lower alkyl, B is a divalent moiety capable of linking amine groups, n is an integer of 3 or more corresponding to the number of the core branches and Z is hydrogen or

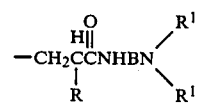

wherein $R^1$ is hydrogen or

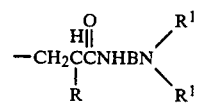

wherein each generation is represented by

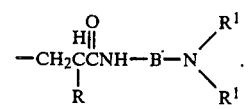

More preferably A is a core such as

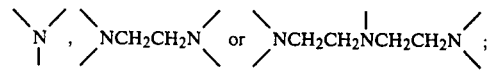

R is hydrogen or methyl; B is the divalent residue of a polyamine, most preferably an alkylene polyamine such as ethylene diamine or a polyalkylene polyamine such as triethylene tetramine; n is an integer from 3 to 2000, more preferably from 3 to 1000, most preferably from 3 to 125, and Z is most preferably

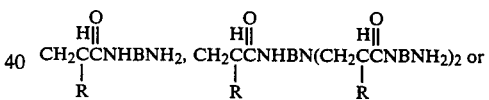

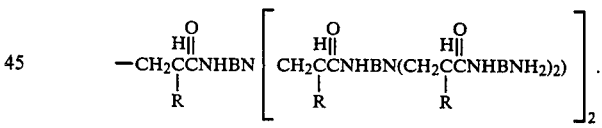

The dense star polymers of this invention are readily prepared by reacting a compound capable of generating a polyvalent core with a compound or compounds which causes propagation of dendritic branches from the core. In one method of preparing these dendrimers (herein called the successive excess reactant method), it is essential to maintain an excess of coreactant to reactive moieties in the terminal groups in the core, core adduct or subsequent adducts and dendrimers in order to prevent cross-linking and to maintain the ordered character of the dendritic branches. In general, this excess of coreactant to reactive moieties in the terminal groups is from about 2:1 to about 120:1, preferably from about 3:1 to about 20:1 on a molar basis.

Alternatively, the compound capable of generating a polyvalent core, $W(X)_n$, wherein W is the polyvalent core atom and is covalently bonded to nX reactive terminal groups ($n \leq 2$), is reacted with a partially protected multifunctional reagent, $T(U) V_m$, wherein U represents a multivalent moiety covalently bonded to m V protected moieties (m≦2), and to one T, a moiety capable of reacting with X to form W[(X'-T')U V $_m$]$_n$, wherein X' and T' represent the residue of reaction between X and X. This first generation compound is then subjected to activation conditions whereby the V moieties are made reactive (deprotected) and reacted with the partially protected multifunctional reagent, T-U-V$_m$, to form the second generation protected dendrimer, W[{(X'-T')U V }$_m$T'-U V $_m$]$_n$. This protected dendrimer can be activated and reacted again in a similar manner to provide the third generation protected dendrimer. Both the successive excess reactant and the partially protected reactant method are specifically illustrated hereinafter.

The successive excess reactant method of preparing the dendrimers is illustrated by the preparation of the aforementiond ternary dendritic polyamidoamine. In this method, ammonia, a nucleophilic core compound, is first reacted with methyl acrylate under conditions sufficient to cause the Michael addition of one molecule of the ammonia to three molecules of the methyl acrylate to form the following core adduct:

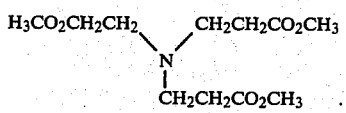

Following removal of unreacted methyl acrylate, this compound is then reacted with excess ethylenediamine under conditions such that one amine group of the ethylenediamine molecule reacts with the methyl carboxylate groups of the core adduct to form a first generation adduct having three amidoamine moieties represented by the formula:

The molar excess of ethylene diamine to methyl acrylate moieties is preferably from 4:1 to 50:1. Following removal of unreacted ethylenediamine, this first generation adduct is then reacted with excess methyl acrylate under Michael's addition conditions to form a second generation adduct having terminal methyl ester moieties:

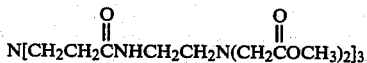

which is then reacted with excess ethylenediamine under amide forming conditions to produce the desired polyamidodiamine dendrimer having ordered, second generation dendritic branchs with terminal amine moieties. The molar excess of coreactant to reactive moieties in each case is preferably from 1.1:1 to about 40:1, most preferably from about 3:1 to about 10:1. Similar dendrimers containing amidoamine moieties can be made by using organic amines as the core compound, e.g. ethylenediamine which produces a tetra-branched dendrimer or diethylenetriamine which produces a penta-branched dendrimer.

Other dendrimers made by the successive excess reactant method are polysulfides made by (1) reacting a polythiol, C(CH$_2$SH)$_4$, under basic conditions with epichlorosulfide to form the first generation polyepisulfide,

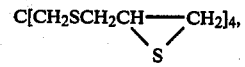

and (2) then reacting this polyepisulfide with hydrogen sulfide to form the first generation polysulfide which can be further reacted with epichlorosulfide and hydrogen sulfide to form subsequent generations. The conditions and procedures which may be suitably employed for polysulfide formation are generally described in Weissberger, *Heterocyclic Compounds with Three-and Four-Membered Rings*, Interscience Publishers, N.Y., 605 (1964) and Meade el al., *J. Chem. Soc.*, 1894 (1948). Polyaminosulfide dendrimers can be prepared by reacting ammonia or an amine having a plurality of primary amine groups with an excess of ethylene silfide to form a polysulfide and then with exces aziridine to form a first generation polyaminosulfide which can be reacted with excess ethylene sulfide and then with excess aziridine to form further generations using general reaction conditions described in U.S. Pat. No. 2,105,845 and Natha et al., J. Am. Chem. Soc., 63, 2361 (1941). The polyether or polysulfide dendrimers can also be prepared by the excess reactant method by reacting hexahalobenzene with phenol of thiophenol to form a first generation polyarylether or polyarylsulfide and then with excess halogen to form the first generation polyhaloarylpolysulfide and then with further phenol or thiophenol to form further generations according to the procedures and conditions as described by D. D. MacNicol el al., *Tetrahedron Letters*, 23, 4131-4 (1982).

Illustrative of the partially protected reactant method, a polyol such as pentaerythritol, C(CH$_2$OH)$_4$, is employed as the polyvalent core generating compound and is converted to alkali metal salt form, e.g., sodium or lithium, by reaction with alkali metal hydroxide or zero valence alkali metal and then reacted with a molar excess of a partially protected compound such as tosylate ester of 1-ethyl-4-hydroxymethyl-2,6,7-trioxabicyclo[2,2,2]octane to form a protected first generation polyether,

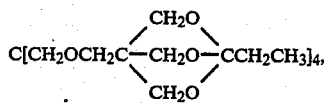

which is then activated by reacting with acid such as hydrochloric acid to form the unproteected first generation polyether, C(CH$_2$O-CH$_2$C[CH$_2$OH]$_3$)$_4$. This polyether is converted to alkali metal salt form by reaction with alkali metal hydroxide or zero valence alkali metal and then reacted with a molar excess of the partially protected tosylate ether to form the protected second generation polyether. The foregoing sequence is repeated as desired for additional generation development according to conditions and procedures described in Endo et al., *J. Polym. Sci.*, Polym. Lett. Ed., 18, 457 (1980), Yokoyama et al., *Macromolecules*, 11-17 (1982), and Pedias et al., *Macromolecules*, 15, 217-223 (1982). These polyether dendrimers are particularly desirable for use in highly alkaline or highly acidic media wherein hydorlysis of a polyamidoamine dendrimer would be unacceptable. As an example of other dendrimers that are suitably prepared by the partially protected reactant method, polyamine dendrimers may be prepared by reacting ammonia or an amine having a plurality of primary amine groups with N-subsstituted aziridine such as N-tosyl aziridine,

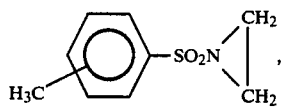

to form a protected first generation polysulfonamide and then activated with acid such as hydrochloric acid to form the first generation polyamine salt and reacted with further N-tosyl aziridine to form the protected second generation polysulfonamide which sequence can be repeated to produce higher generation polyamines using the general reaction conditions described in Humrichause, C. P., PhD, Thesis from University of Pennsylvania, "N-Substituted Aziridines as Alkylating Agents", Ref. No. 66-10, 624 (1966).

In either of the foregoing methods of dendrimer preparation, water or hydrogen sulfide may be employed as nucleophilic cores for the production of binary dendrimers. Examples of other nucleophilic core compounds include phosphine, polyalkylene polyamines such as diethylenetriamine, triethylenetetramine, tetraethylenepentamine and both linear and branched polyethyleimine; primary amines such as methylamine, hydroxyethylamine, octadecylamine and polymethlenediamines such as hexamethylenediamine; polylaminoalkylarenes such as 1,3,5-tris(aminomethyl)benzene; tris(aminoalkyl)amines such as tris(aminoethyl)amine; heterocyclic amines such as imidazolines and piperidines; and various other amines such as hydroxyethylaminoethylamine, mercaptoethylamine, morpholine, piperazine, amino derivatives of polyvinylbenzyl chloride and other benzylic polyamines such as tris(1,3,5-aminomethyl)benzene. Other suitable nucleophilic cores include polyols such as the aforementioned pentaerythritol, ethylene glycol and polyalkylene polyols such as polyethylene glycol and polypropylene glycol; 1,2-dimercaptoethane and polyalkylene polymercaptans; thiophenols, and phenols. Of the core compounds, ammonia and the polyalkylene polyamines are preferred for the preparation of polyamidoamine dendrimers by the successive excess reactant method and the polyols are preferred for the preparation of polyether dendrimers by the partially protected reactant method.

Examples of coreactant materials used to react with the nucleophilic core compounds include $\alpha,\beta$-ethylenically unsaturated carboxylic esters and amides such as methyl acrylate, ethyl acrylate, acrylonitrile, methyl itaconate, dimethyl fumarates, maleic anhydride, acrylamide, as well as esters, acids and nitriles containing an acrylyl moiety, with methyl acrylate being the preferred coreactant material. In general other preferred unsaturated reactants are volatile or otherwise readily removed from the core/coreactant reaction products without deleteriously affecting the reaction product.

Examples of the second coreactant materials used to react with the adduct of the nucleophilic core and the first coreactant include various polyamines such as alkylene polyamines and polyalkylene polyamines such as ethylenediamine and diethylenetriamine; benzylic polyamines such as tris(1,3,5-aminomethyl)benzene; alkanolamines such as ethanolamine; and aziridine and derivatives thereof such as N-aminoethyl aziridine. Of these second coreactant materials, the volatile polyamines such as ethylenediamine and diethylenetriamine are preferred, with ethylenediamine being especially preferred.

Alternatively, the dendrimers can be prepared by reacting an electrophilic core such as a polyester with a coreactant such as a polyamine to form a core adduct which is then reacted with a suitable second coreactant such as an unsaturated ester to form the first generation polyamidoamine. Thereafter, this first generation product is reacted with a suitable third coreactant such as polyamine and then with the second coreactant such as unsaturated ester to form the desired second generation dendrimer. Examples of suitable electrophilic cores include the $C_1$–$C_4$ alkyl esters of various polycarboxylic acids such as benzene tricarboxylic acid, oxalic acid, terphthalic acid and various other carboxylic acids represented by the formula:

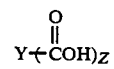

wherein Y is hydrocarbyl or a hydrocarbon polyl wherein the hydrocarbon radical is alkyl, aryl, cycloalkyl, alkylene, arylene, cycloalkylene, and corresponding trivalent, tetravalent, pentavalent and hexavalent radicals of such hydrocarbons; and Z is a whole number from 1 to 6. Preferred electrophilic cores include poly(methyl acrylates), poly(acryloyl chloride), poly(methacryloyl chloride), alkyl acrylate/alkyl methacrylate copolymers, polymers of alkyl fumarates, and polymers of alkyl itaconates. Of the electrophilic cores, alkyl acrylate/alkyl methacrylate copolymers and alkyl acrylate/alkyl itaconate copolymers are most preferred.

Suitable first coreactants for reaction with the electrophilic core include polyalkylene polyamines such as ethylenediamine, diethylenetriamine, triethylenetetramine and other polyamines represented by the formula:

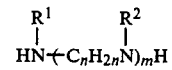

wherein $R^1$ and $R^2$ independently represent hydrogen or an alkyl, preferably $C_1$–$C_4$ alkyl, hydroxyalkyl, cyanoalkyl, or amido; n is at least 2 and preferably 2 to 6 and m is 2 to 100, preferably 2 to 5. Examples of suitable second coreactants to be used in preparing dendrimers from electrophilic cores include alkyl esters of ethylenically unsaturated carboxylic acids such as methyl acrylate, methyl methacrylate, ethyl acrylate and the like. Examples of suitable third coreactants are those illustrated for the first coreactant.

Thus prepared, the dendrimers can be reacted with a wide variety of compounds to produce the polyfunctional compounds having the unique characteristics that are attributable to the structure of the dendrimer. For example, a dendrimer having terminal amine moieties, as in the polyamidoamine dendrimer, may be reacted with an unsaturated nitrile to yield a polynitrile (nitrile-terminated) dendrimer. Alternatively, the polyamidoamine dendrimer may be reacted with (1) an $\alpha,\beta$-ethylenically unsaturated amide to form a polyamide (amide-terminated) dendrimer (2) an $\alpha,\beta$-ethylenically unsaturated ester to form a polyester (ester-terminated)

dendrimer, (3) an oxirane to yield a polyol (hydroxy-terminated) dendrimer, or (4) an ethylenically unsaturated sulfide to yield a polymercapto (thiol-terminated) dendrimer. In addition, the dendrimer may be reacted with an appropriate difunctional or trifunctional compound such as an alkyl dihalide or an aromatic diisocyanate to form a poly(dendrimer) or bridged dendrimer having a plurality of dendrimers linked together through the residues of the polyhalide or polyisocyanate. The bridged dendrimers can also be prepared by (1) reducing the amount of coreactive material, e.g., the polyamine in polyamidoamine dendrimers, employed to a molar ratio in the range from about 5 to about 10 moles of coreactive material per mole of reactive terminal groups on the dendrimer and (2) exposing the dendrimers to higher temperatures, e.g., from about 200° C. to about 150° C., in the presence of the coreactive material. Dendrimer bridging also results when amine-terminated dendrimer is mixed with ester-terminated dendrimer under amidation conditions.

Such reactions are further exemplified by the following working examples. In such working examples, all parts and percentages are by weight unless otherwise indicated.

EXAMPLE 1

A. Preparation of Core Adduct

To a one-liter, 3-neck flask equipped with stirrer, condenser and thermowell, and containing methyl acrylate (296.5 g, 3.45 moles) is added at room temperature with stirring over a 6-hour period ammonia (8.7 g, 0.58 mole) dissolved in 102.2 g of methanol. The mixture is allowed to stand at room temperature for 48 hours at which point excess methyl acrylate is removed by vacuum distillation (1 mmHg at 22° C.) yielding 156 g of residue. This residue is analyzed by size exclusion chromatography ($C_{13}$ NMR) and liquid chromatography. This analysis indicates the coreactant adduct to be the Michael's addition product of 1 mole of ammonia and 3 moles of methyl acrylate at a 97.8 percent yield.

B. Preparation of First Generation Adduct

To ethylenediamine (505.8 g, 8.43 moles) dissolved in 215.4 g of methanol in a 3-liter reaction flask equipped with stirrer, condenser and thermowell, is added the aforementioned ammonia/methyl acrylate adduct (28.1 g, 0.1022 mole), and the reaction mixture is allowed to stand at room temperature for 55 hours. The resulting mixture (747.6 g) is subjected to vacuum distillation to remove excess ethylenediamine and methanol at 2 mmHg and 72° C. The residue (35.4 g) is analyzed by size exclusion chromatography and other suitable analytical techniques. The analyses indicates that essentially all of the ester moieties of the ammonia/methyl acrylate adduct had been converted to amides in the form of a compound represented by the following structural formula:

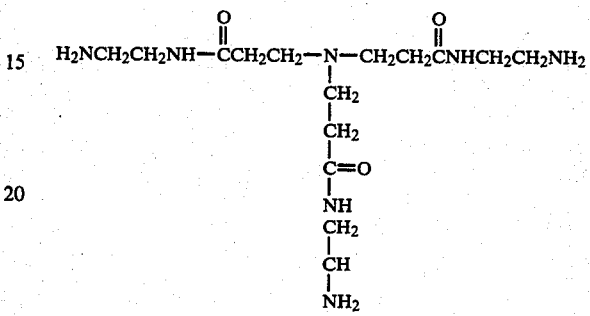

thus indicating a yield of 98.6 percent.

C. Preparation of Second Generation Polyester Dendrimer

To methyl acrylate (93.2 g, 1.084 moles) in a one-liter flask equipped with condenser, stirrer and thermowell, and heated to 32° C. is added the aforementioned first generation adduct (18 g, 0.0501 mole) dissolved in 58.1 g of methanol over 1.5 hours. The resulting mixture is maintained at 32° C. for an additional 5 hours and allowed to stand an additional 18 hours at room temperature. The reaction mixture (165.7 g) is stripped of methanol and excess methyl acrylate by vacuum distillation (2 mm Hg and 50° C.) to produce 43.1 g of residue. Analysis by suitable techniques indicates the product to be a second generation polyester dendrimer represented by the following formula:

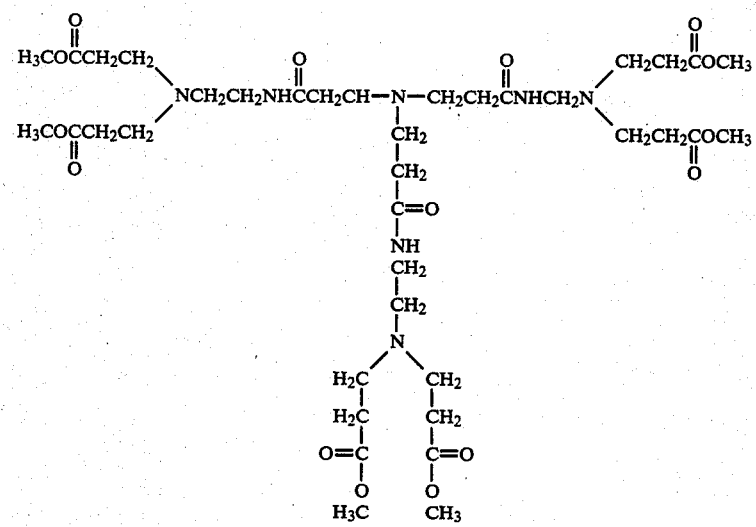

in 98.4 percent yield.

D. Preparation of Second Generation Polyamine Dendrimer

To ethylenediamine (328.8 g, 5.48 moles) dissolved in 210.2 g of methanol at room temperature in the aforementioned flask is added with stirring the second generation polyester dendrimer (34.9 g, 0.0398 mole) dissolved in 45.3 g of methanol. The resulting mixture is allowed to stand for 66 hours at room temperature at which time excess ethylenediamine and methanol is stripped from the product by vacuum distillation (2 mm Hg at 72° C.) to yield 41.1 g (99.0 percent yield) of product. This product is determined by size exclusion chromatography to be the second generation polyamine of the aforementioned polyester dendrimer.

E. Preparation of Third Generation Polyester Dendrimer

To methyl acrylate (65.1 g, 0.757 mole) is added the aforementioned second generation polyamine dendrimer (28.4 g, 0.0272 mole) dissolved in 84.6 g of methanol over a period of 1 hour and 15 minutes. The resulting mixture is allowed to stand for 18 hours at 25° C. after which time excess methyl acrylate and methanol are removed by vacuum distillation (2 mm Hg at 50° C.) to yield 56.3 g (100.0 percent yield) of product residue. Analysis of this residue by suitable analytical techniques indicate that it is a third generation polyester dendrimer having 3 core branches with 4 terminal ester moieties per core branch thereby providing 12 terminal ester moieties per dendrimer molecule.

F. Preparation of Third Generation Polyamine Dendrimer

To ethylenediamine (437.6 g, 7.29 moles) dissolved in 192 g of methanol is added the aforementioned third generation polyester dendrimer (44.9 g, 0.0216 mole) dissolved in 69.7 g of methanol. The addition occurs over a period of 48 hours at 25° C. with stirring. The resulting reaction mixture is then allowed to stand for 19 hours at 25° C. after which time excess methanol and ethylenediamine are removed by vacuum distillation (2 mm Hg at 72° C.) to yield 51.2 g of residual product. Analysis of this residue indicates a yield of 85.3 percent of a third generation polyamine dendrimer having 3 core branches with 4 terminal primary amine moieties per core branch, thereby providing 12 terminal primary amine moieties per molecule of dendrimer. This dendrimer is calculated to have a molecular volume of 50,000 to 97,000 cubic A and a density of a terminal amine moiety of 1 to 3($\times 10^{-4}$) moieties/cubic A.

EXAMPLE 2

Following the procedure of Example 1, except that a molar equivalent amount of ethylenediamine is substituted for ammonia as the core compound, a third generation polyamine dendrimer is prepared. Upon analysis, it is determined that this dendrimer has four core branches with 4 terminal primary amine moieties per core branch, thereby providing 16 terminal primary amine moieties per molecular of dendrimer. This dendrimer has a molecular volume of 60,000 to 120,000 cubic A and a terminal amine density of 2 to 6($\times 10^{-4}$) amines/cubic A.

Similar dendrimers are obtained when equimolar amounts of 1,2-diaminopropane, 1,3-diaminopropane and 1,6-diaminohexane (hexamethylenediamine) are substituted for the ethylenediamine as the core compound in the foregoing procedure. When an equimolar amount of dodecylamine or benzylamine is substituted for the ethylenediamine as the core compound, the resulting dense star polymers have 2 core branches per molecule with 4 terminal primary amine groups per branch, thereby providing a total of 8 primary amine groups per polymer molecule. Substitution of triaminoethylamine for ethylenediamine as the core compound yields a dendrimer having 6 core branches with 4 terminal primary amine moieties per core branch, thereby providing 24 terminal primary amine moieties per molecule of dendrimer.

EXAMPLE 3

A. First Amidation

Following the procedure of Example 1, 5 g (0.0198 mole) of trimethyl-1,3,5-benzenetricarboxylate is mixed with 6.3 g (0.0368 mole) of aminoethylethanolamine ($NH_2CH_2CH_2NHCH_2CH_2OH$) to form a white paste. This mixture is heated at 120° C. for 3 hours to form 9.48 g of a light yellow syrup which infrared and nuclear magnetic resonance spectral analysis indicated is an amidoamine represented by the structural formula:

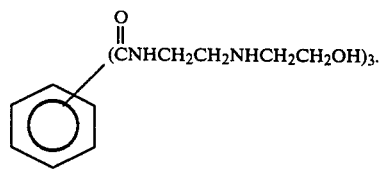

1,3,5-isomer

B. First Alkylation

A 9.48 g (0.0202 mole) of this amidoamine is combined with a stoichiometric excess (11.0 g, 0.127 mole) of methyl acrylate and heated for 24 hours at 80° C. which, after devolatilization, is a light yellow syrup weighing 14.66 g. Nuclear magnetic resonance ($H^1$) and infrared spectral analysis of the syrup indicates that it is a triester represented by the structural formula:

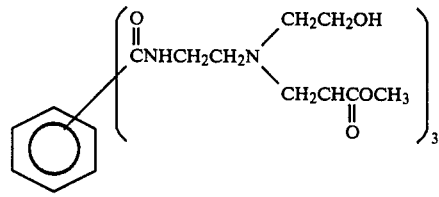

1,3,5-isomer

C. Second Amidation

Following the procedure of part A of this example, the triester (4.57 g, 6.3 × 10$^{-3}$ mole) produced in part B is mixed with 1.96 g (1.89 × 10$^{-2}$ mole) of aminoethylethanolamine and heated at 90° C. for 48 hours to form 5.8 g of a light yellow, highly viscous syrup. Analysis of this product by nuclear magnetic resonance ($H^1$) (DMSO-$d_6$) and infrared spectroscopy indicates that it is a triamidoamine represented by the structural formula:

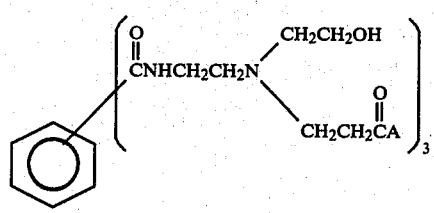

wherein each A is individually

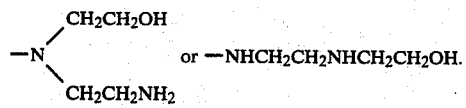

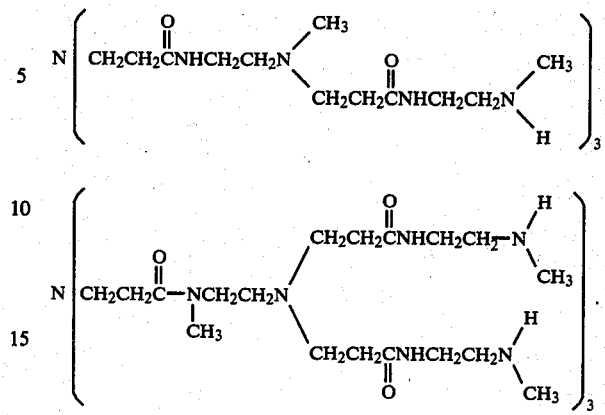

EXAMPLE 4

A. First Amidation

A 27.3-g portion (0.1 mole) of a triester represented by the formula:

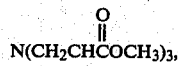

is mixed with 30 g (0.405 mole) of N-methyl ethylenediamine (MEDA) and 16.6 g of methanol and then heated at 63° C. for 11 hours. The product is then stripped of unreacted MEDA and methanol to yield 36.1 g of a triamide represented by the formula:

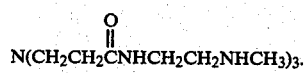

B. First Alkylation

To the aforementioned triamide (36.1 g, 0.09 mole) is added 38.5 g of methanol to yield a clear solution to which is added 50.5 g (0.59 mole) of methyl acrylate dropwise over a period of 2 hours at 38° C. The temperature of the resulting mixture is increased to 53° C. for 5 additional hours after which unreacted methyl acrylate and methanol are removed under vacuum to yield 61 g of a light yellow syrup. Analysis of this product by nuclear magnetic resonance ($H^1$) spectroscopy indicates that it is represented by the formula:

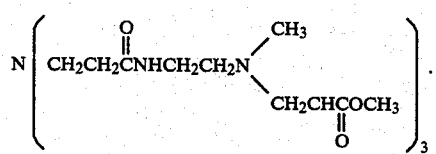

C. Second Amidation

To 60.8 g of the aforementioned first alkylation product are added with stirring 42.7 g of methanol and 26.6 g (0.359 mole) of MEDA followed by heating the resulting mixture at 65° C. for 6 hours. Vacuum stripping of the mixture yields 72.7 g of light yellow syrup. Analysis of this product (syrup) indicates that it is a mixture of isomers having the following structures:

D. Second Alkylation and Third Amidation

Alkylation of the aforementioned second amidation product with methyl acrylate and then amidation of the resulting alkylated product with MEDA in accordance with aforementioned procedures yield a mixture of isomers having core branches with dendritic characteristics.

EXAMPLE 5

Demulsification Method

To 100 ml of an oil-in-water emulsion containing about 5 percent of crude oil having a specific gravity of ~0.98 g/ml is added one part per million based on the emulsion of the dendrimer (ethylene diamine core) of Example 2. The emulsion is then shaken for 3 minutes to effectively disperse the dendrimer into the emulsion. The emulsion is allowed to stand for 10 minutes and visually evaluated. After 10 minutes, the emulsion appears to be completely resolved into two phases having a distinct interface wherein the aqueous phase is essentially transparent.

Following the foregoing procedure except substituting a quaternized form of the foregoing dendrimer for the dendrimer, the emulsion is similarly resolved using 0.5 ppm and 1 ppm of the quaternized form. This quaternized form is prepared by reacting the 32.42 g (0.01 mole) of the dendrimer in 100 ml of methanol with 24.32 g (0.16 mole) of 2-hydroxy-3-chloropropyl trimethyl ammonium chloride in 30 ml of water at 50° C. for about 12 hours.

What is claimed is:

1. A dense star polymer having at least one core branch emanating from a core, each core branch having at least one terminal group provided that (1) the ratio of terminal groups to the branches emanating from the core is 2:1 or greater, (2) the density of terminal groups in the dense star polymer is at least 1.5 times that of a conventional star polymer having similar core and monomeric moieties and a comparable molecular weight and number of core branches wherein each of such branches of the conventional star polymer bears only one terminal group, (3) a molecular volume that is equal to or less than 60 percent of the molecular volume of said conventional star polymer, and (4) the two-dimensional molecular diameter of the dense star polymer is in the range from about 12 to about 2000 Angstrom units.

2. The dense star polymer of claim 1 having (1) at least 2 core branches per core, (2) a terminal group density at least 5 times that of the corresponding conventional star polymer, (3) a molecular volume that is equal to or less than 50 percent of the volume of the conventional star polymer, and (4) the two-dimensional molecular diameter of the dense star polymer is in the range from about 25 to about 500 Angstrom units.

3. The polymer of claim 1 which is a dendrimer having a polyvalent core that is covalently bonded to at least 1 ordered dendritic branch which extends to two generations such that each dendritic branch has at least four terminal groups and a symmetrical structure.

4. The dense star polymer of claim 2 having at least 3 core branches per core.

5. The dense star polymer of claim 4 which is a polyether wherein the core is derived from a polyol and the core branches have ether linkages.

6. The dense star polymer of claim 2 which is a polyether wherein the core is derived from a polyol and the core branches have ether linkages.

7. A dendrimer having (1) a polyvalent core derived from ethylene glycol, or a polyalkylene polyol and (2) at least two ordered dendritic core branches which (a) are covalently bonded to the polyvalent core, (b) extend through at least two generations, and (c) have at least 3 terminal groups per core branch.

* * * * *